(12) United States Patent
Lorenzoni et al.

(10) Patent No.: US 8,575,413 B2
(45) Date of Patent: Nov. 5, 2013

(54) PROCESS FOR THE ALKYLATION OF BENZENE WITH ISOPROPANOL OR BLENDS OF ISOPROPANOL AND PROPYLENE

(75) Inventors: Loreno Lorenzoni, Porto Torres (IT); Paolo Calaresu, Sassari (IT); Pier Gianni Cabras, Sassari (IT)

(73) Assignee: Polimeri Europa S.p.A., San Donato Milanese (IT)

( * ) Notice: Subject to any disclaimer, the term of this patent is extended or adjusted under 35 U.S.C. 154(b) by 187 days.

(21) Appl. No.: 13/063,244

(22) PCT Filed: Sep. 7, 2009

(86) PCT No.: PCT/IB2009/006782
§ 371 (c)(1),
(2), (4) Date: May 27, 2011

(87) PCT Pub. No.: WO2010/029405
PCT Pub. Date: Mar. 18, 2010

(65) Prior Publication Data
US 2011/0218366 A1   Sep. 8, 2011

(30) Foreign Application Priority Data
Sep. 11, 2008   (IT) .............. MI2008A1625

(51) Int. Cl.
  C07C 2/86     (2006.01)
  C07C 37/08    (2006.01)
(52) U.S. Cl.
  USPC ................. 585/446; 585/469; 568/798

(58) Field of Classification Search
None
See application file for complete search history.

(56) References Cited

U.S. PATENT DOCUMENTS

| 5,015,786 A | 5/1991 | Araki et al. |
| 6,512,153 B1 | 1/2003 | Cappellazzo et al. |

FOREIGN PATENT DOCUMENTS

| EP | 0 432 814 | 6/1991 |
| EP | 1 069 099 | 1/2001 |

OTHER PUBLICATIONS

Wichterlova et al., Microporous Materials (1996), 6(5-6), p. 405-414.*
Reddy, K. S. N. et al., "Alkylation of Benzene With Isopropanol Over Zeolite Beta", Applied Catalysis A; General, vol. 95, pp. 53-63, XP008067633, ISSN: 0926-860X, (Jan. 1, 1993).
International Search Report issued May 7, 2010 in PCT/IB09/006782 filed Sep. 7, 2009.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The invention relates to a process for the alkylation of benzene with isopropanol (IPA) as alkylating agent, or blends of isopropanol and propylene, which comprises effecting said reaction completely in gaseous phase and in the presence of a catalytic system containing a zeolite belonging to the MTW family.

18 Claims, 1 Drawing Sheet

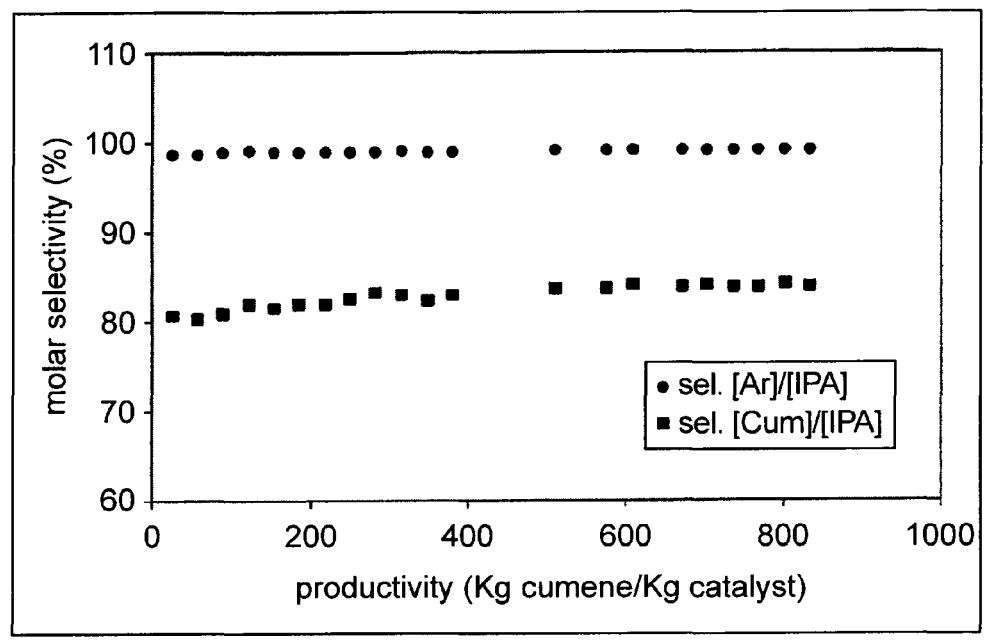
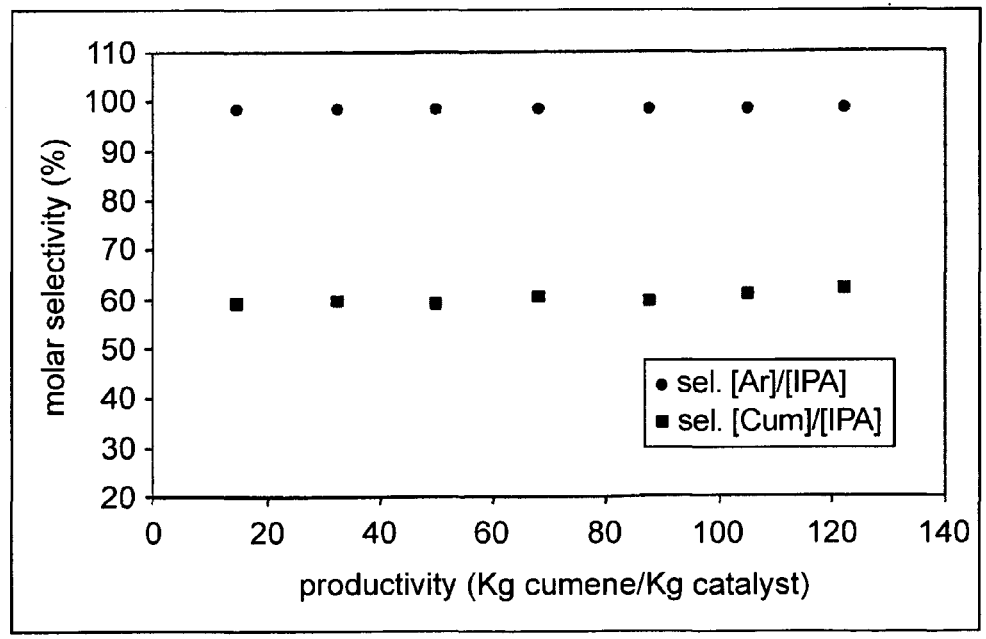

PROCESS FOR THE ALKYLATION OF BENZENE WITH ISOPROPANOL OR BLENDS OF ISOPROPANOL AND PROPYLENE

The present invention relates to a process for the alkylation of benzene with isopropanol (IPA) as alkylating agent, or blends of isopropanol and propylene, which comprises effecting said reaction completely in gaseous phase and in the presence of a catalytic system containing a zeolite belonging to the MTW family.

The process is characterized by the absence of negative effects on the performance and life of the catalyst due to the presence of high quantities of water in the reaction blend in addition to by-products deriving from undesired reactions, and it also provides much higher productivities with respect to those provided by catalysts of the prior art used for the same process.

The absence of negative effects is due to the particular catalytic system used, which proves to be particularly suitable for the alkylation of benzene with the alkylating agent isopropanol, or blends of isopropanol and propylene, under the selected reaction conditions.

The invention also relates to a process for preparing phenol wherein the first step for the preparation of cumene is effected by the alkylation of benzene according to what is specified above.

Cumene is an important precursor for the production of phenol, in turn useful as intermediate for the preparation of caprolactam from which nylon is produced.

The complete process for the preparation of phenol comprises the alkylation of benzene to cumene, the oxidation of cumene to the corresponding hydroperoxide which, by acid treatment generates phenol and acetone.

As far as the first alkylation step is concerned, in addition to zeolite catalysts, catalysts based on phosphoric acid and diatomaceous earth for fixed bed reactors or $AlCl_3$ in slurry, are still partially used, in the petrochemical industry. In all cases, the alkylation reaction of benzene with propylene is carried out under reaction conditions corresponding to a complete liquid phase of the reagent blend.

Problems relating to environmental impact and safety, however, are present in processes based on the use of catalysts based on phosphoric acid and $AlCl_3$: the use of these catalysts, in fact, is particularly complicated due to corrosion, the by-production of toxic organic products and the disposal of the exhausted catalysts.

In 1965, the preparation of cumene was described for the first time using zeolite X or zeolite Y as catalyst (Fnachev, Kr. M., et al, Nefiekhimiya 5 (1965) 676).

Subsequently, the use of zeolites having a faujasite structure for the alkylation of benzene with light olefins, such as propylene, were described by Venuto et al. (J. Catal. 5, (1966) 81).

In the synthesis of cumene, optimum results have been obtained, in terms of industrial application, using zeolites with a beta structure, as described in EP 432814, in particular using catalysts comprising beta zeolite according to what is described in EP 687500.

Once obtained, the cumene is transformed into phenol by means of an oxidation step to cumyl hydroperoxide, followed by an acid treatment step which causes the breakage of the peroxide bond with the formation of phenol and acetone.

If, on the one hand, the simultaneous production of phenol and acetone in a single production unit certainly represents a positive aspect from an industrial point of view, on the other hand, the unbalanced commercial demand for the two products can represent a problem in the management of an industrial plant for the production of phenol.

It should in fact be remembered that for every kg of phenol produced from cumene according to the traditional process via propylene, 0.61 kg of acetone are also produced.

Considering that one of the major uses of acetone is represented by methyl methacrylate (MMA), for which the demand on the market is decreasing, whereas the demand for Bisphenol A (BPA), phenolic resins and caprolactam, main downstream uses of phenol, is increasing, the potential problem caused by the co-production of acetone in the production of phenol via cumene can be easily understood.

The necessity is therefore strongly felt to find a possible alternative use which allows a convenient exploitation of acetone, when the market conditions are such as to discourage its direct sale.

U.S. Pat. No. 5,017,729 describes a process for the production of phenol via cumene hydroperoxide characterized by the use of propylene, in the cumene preparation step, partially or totally deriving from the reduction of acetone (co-produced with phenol) with hydrogen and the subsequent dehydration of isopropyl alcohol.

In this process, the high cost of the various steps dedicated to re-obtaining pure propylene—to be used in the alkylation step—starting from acetone co-produced with phenol, is evident.

In particular, in the process proposed by Mitsui (PEP Review 95-1-1 1) for the production of propylene starting from acetone, in fact, the higher investment cost can be ascribed to the de-hydration section of isopropyl alcohol—obtained from acetone in the relative reduction section with hydrogen—to propylene.

The dehydration step of IPA to propylene is necessary, on the other hand, for the purposes of a concrete industrial application, due to the extreme difficulty in carrying out the alkylation of benzene directly with isopropyl alcohol as alkylating agent when acid catalysts of the conventional type are used, as a result of the water released by the IPA during the reaction which produces negative effects on the performances of the catalyst in terms of selectivity, but above all duration of the catalyst itself.

Acid catalysts of both the zeolitic and non-zeolitic type, are in fact negatively influenced by the presence of the water formed when isopropyl alcohol is used as alkylating agent of benzene to give cumene.

In the case of a catalyst of the conventional type such as phosphoric acid, for example, supported on silica, widely used in the industrial synthesis of cumene, quantities of water higher than a few hundreds of ppm in the reaction mixture produce a significant chemical and mechanical disgregation of the catalyst, together with a considerable reduction in the catalytic performances in terms of yield to cumene.

In the case of zeolite-based catalysts, the negative effect due to the presence of water which is revealed by a lowering of the overall yield to cumene together with a more or less rapid deactivation of the catalyst itself, is known.

All of these negative effects are however known and also verified with very low contents of water—present in the reaction—with respect to those obtained using isopropyl alcohol as alkylating agent of benzene to give cumene in a concrete industrially applicable process.

The industrial applicability of an alkylation process of benzene with isopropyl alcohol, in fact, cannot disregard certain parameters such as, for example, the benzene/IPA molar ratio in the feeding to the reaction section, which generally ranges from 4 to 8 with a corresponding concentration of water in the reaction equal to about 48,000 and 26,000 ppm assuming the total conversion of the isopropyl alcohol.

Even effecting the alkylation of benzene with an alkylating agent consisting of a mixture of isopropanol and propylene would in any case require considerably reducing the quantity of isopropyl alcohol used for guaranteeing a water content which could be tolerated by the catalytic system thus limiting the actual potentiality of the same process.

The catalysts used for the alkylation of benzene with propylene cannot always be easily adapted to the alkylation reaction of benzene with isopropyl alcohol, or mixtures of isopropyl alcohol and propylene, as alkylating agent, as these catalysts are generally extremely sensitive to water and consequently their life in the presence of the water formed by the dehydration of the isopropanol is extremely reduced.

The possibility of alkylating benzene with isopropyl alcohol using beta zeolite as catalyst, in gas phase, preferably at atmospheric pressure, has also been described (K. S. N. Reddy et al., Applied Catalysis A: General, 95 (1993) 53-63). Also in this case, the deterioration of the catalyst, also observed with high benzene/isopropanol ratios, is evident.

In experimental tests described in the reference cited above, problems of the duration of the catalyst with the progress of the experimental tests, are revealed.

U.S. Pat. No. 5,015,786 describes a process for the production of phenol via cumene in which part of the cumene derives from the alkylation of benzene, also effected with isopropyl alcohol obtained by the reduction of the acetone co-produced with the phenol, together with cumene deriving from the alkylation of benzene with propylene.

The alkylation step of benzene with IPA is carried out in the presence of a catalyst of an acid nature, selected from various materials: zeolites are indicated as preferred catalysts. It is interesting to note, however, that in the above document there is no information on the life of the catalyst and in general on the constancy of the performances considering that the longest test lasts 200 hours (Ex. 5, column 15) which correspond, under the conditions given, to a productivity not higher than about 100 Kg Cumene/Kg of catalyst.

In order to overcome the problems mentioned above, the use of particular zeolites with marked hydrophobic characteristics has been proposed, such as ZSM-5 zeolite with a high silica/alumina ratio or H-mordenite and dealuminated Y zeolite.

In U.S. Pat. No. 5,160,497, for example, a dealuminated Y zeolite is used, with an $SiO_2/Al_2O_3$ molar ratio ranging from 8 to 70, for the alkylation of benzene with propylene and isopropanol.

EP 1069100 describes a process for the alkylation of benzene with isopropanol, optionally in a blend with propylene, which consists in effecting said reaction under mixed gas-liquid phase conditions or under completely liquid phase conditions, at temperatures and pressures which are such that the concentration of water in the liquid reaction phase is not higher than 8,000 ppm weight/weight, regardless of the total water content present in the reaction mixture. The catalyst is of the zeolitic type and is preferably selected from beta zeolite, Y zeolite, ZSM-12 and mordenite.

EP 1069099 describes a process for the alkylation of benzene with isopropanol, or mixtures of isopropanol and propylene, under pressure and temperature conditions corresponding to complete gas phase of the mixture present in the reaction section and in the presence of a catalyst comprising beta zeolite and an inorganic ligand.

BRIEF DESCRIPTION OF THE DRAWINGS

FIG. 1 is a graph of molar selectivity versus productivity of the catalyst of Example 1.

FIG. 2 is a graph of molar selectivity versus productivity of the catalyst of Example 2.

We have now found that it is possible to obtain cumene by the alkylation of benzene with isopropanol (IPA), as alkylating agent, or blends of isopropanol and propylene, by means of a process which provides better results in terms of performances, duration of the catalyst and consequently productivity, even in the presence of considerable quantities of water, operating under suitable reaction conditions and using a catalyst comprising a catalyst of the MTW type.

An object of the present invention therefore relates to a process for the alkylation of benzene with isopropanol, or a blend of isopropanol and propylene, which comprises effecting said reaction completely in gaseous phase and in the presence of a catalytic system containing a zeolite belonging to the MTW family: in accordance with this, the reaction conditions correspond to complete gas phase of the reagents, i.e. the process is effected under pressure and temperature conditions which are such as to have the reagents exclusively present in gaseous phase.

According to an aspect of the present invention, it is possible to select pressure and temperature conditions which also correspond to complete gas phase of the whole mixture present in the reaction section: in this case therefore not only are the reagents in gas phase, but also the products.

According to another aspect of the present invention, it is possible to select temperature and pressure conditions which also correspond to at least partial liquid phase of the reaction products: in this case therefore the reagents are in gas phase, whereas the products are at least partially liquid.

The process according to the present invention enables molar ratios between benzene and isopropyl alcohol to be adopted in the feeding to the reaction section which are also much lower than those used in the prior art, within a range of concrete industrial applicability, and therefore regardless of the total quantity of water formed during the reaction.

Zeolites of the MTW structural type which can be used in said invention are for example:: ZSM-12, CZH-5, Nu-13, Theta-3 and TPZ-12. CZH-5 zeolite is described in GB 2079735A; Nu-1 is described in EP59059; Theta-3 is described in EP 162719 and TPZ-12 in U.S. Pat. No. 4,557, 919. The zeolite of the MTW structural type preferably used is a silico-aluminate with a $SiO_2/Al_2O_3$ molar ratio greater than or equal to 20. This zeolite is described in A Katovic and G. Giordano, Chem. Ind. (Dekker) (Synthesis of Porous Materials) 1997 69, 127-137. The aluminum can be either totally or partially substituted by B, Ga, Fe or mixtures thereof, as described by Toktarev & Ione, in Chon et al., Progress in Zeolites and Microporous Material, SSSC, vol. 105, 1997. According to a preferred aspect of the present patent application, ZSM-12 zeolite is used, which is a porous crystalline material having in its calcined and anhydrous form a molar composition of the oxides corresponding to the following formula:

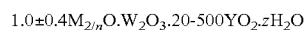

$$1.0 \pm 0.4 M_{2/n}O \cdot W_2O_3 \cdot 20\text{-}500 YO_2 \cdot zH_2O$$

wherein M is $H^+$ and/or a cation of an alkaline or alkaline earth metal having a valence n, W is selected from aluminum, gallium or mixtures thereof, Y is selected from silicon and germanium, z ranges from 0 to 60. M is preferably selected from sodium, potassium, hydrogen or mixtures thereof. W is preferably aluminum and Y is preferably silicon. W can be at least partially substituted by boron, iron or mixtures thereof. ZSM-12 zeolite is described in U.S. Pat. No. 3,832,449, in Ernst et al., Zeolites, 1987, Vol. 7, September, and in Toktarev & Ione, Chon et al., Progress in Zeolites and Microporous Material, SSSC, Vol. 105, 1997.

The MTW zeolite, and in particular ZSM-12 zeolite, is preferably used in the form in which the cationic sites present in its structure are occupied for at least 50% by hydrogen ions. It is especially preferred for at least 90% of the cationic sites to be occupied by hydrogen ions.

According to an aspect of the invention, phosphorous can be added to the MTW zeolite. The addition can be effected by treatment of the zeolite, preferably in ammonia form, with a compound of phosphorous using any of the known techniques, such as mechanical mixing, impregnation or deposition in vapour phase. The phosphorous compound can be selected from the corresponding salts, acids and organic compounds, such as for example alkoxides. The impregnation technique is preferably used, i.e. the zeolite is preferably treated in ammonia form, with an aqueous solution of a compound of P. The resulting suspension, after being kept under stirring, is dried under vacuum at a temperature which is sufficient for eliminating the solvent. The modes and conditions for effecting the impregnation are known to experts in the field. The solid resulting from the drying is then calcined at a temperature ranging from 400 to 600° C. for 1-10 hours. The P is preferably present in a quantity of less than 3% with respect to the total weight of the catalytic composition, and preferably in a quantity higher than or equal to 0.05% and lower than or equal to 2% by weight with respect to the total weight of the catalytic composition.

In the process of the present invention, the zeolite can be used as such or in the form bound with an inorganic ligand. It can be used in the form of pellets obtained by extrusion, for example, or in the form of microspheres obtained by means of spray-drying, these techniques also being applied to the zeolite as such or mixed with a suitable inorganic ligand. The ligand can be alumina, silica, a silico-aluminate, titania, zirconia or clay. The ligand is preferably alumina. In the bound catalyst, the zeolite and ligand can be in a weight ratio ranging from 5/95 to 95/5, preferably from 20/80 to 80/20. In a preferred embodiment, the end-catalyst is also characterized by particular characteristics of extrazeolite porosity, i.e. the porosity fraction of the catalyst which cannot be attributed to the quality and quantity of zeolite present in the end-catalyst. In particular, said extrazeolite porosity has values not lower than 0.4 ml/g of end-catalyst associated with a fraction equal to at least 50% of said extrazeolite porosity with pores having a diameter greater than 100 Angstrom. Said extrazeolite porosity can be obtained with conventional preparation methods and is correctly determined according to known methods described for example in Loweel, Seymour "Introduction to powder surface area", Wiley Interscience.

According to a preferred aspect of the process of the present invention, the operating temperature ranges from 150° C. to 230° C., with a reaction pressure ranging from 1 to 20 bar and in any case under such conditions as to have the reagents present in completely gaseous phase and indifferently using isopropanol or mixtures of isopropanol and propylene as alkylating agent.

It is preferable to operate at a pressure lower than 10 bar, preferably between 5 and 9 bar.

In the processed claimed herein, the molar ratio between benzene and isopropanol preferably varies from 2 to 10, even more preferably from 2 to 4.

When propylene is also used additionally as alkylating agent together with isopropanol, the molar ratio between benzene and alkylating agent—isopropanol plus propylene—preferably ranges from 2 to 10, more preferably from 2 to 4. The molar ratio between isopropanol and propylene preferably varies from 10 to 0.01 and even more preferably from 5 to 0.1.

The alkylation of benzene with isopropanol can be effected in continuous, semi-continuous or batchwise.

When the process is carried out in continuous, it is also possible to operate using a configuration of the reaction system which includes the partial recycling to the reaction section of the organic phase of the effluent leaving the same reaction section, after cooling, demixing and removal of the aqueous phase from the organic phase.

The alkylation reaction of benzene with IPA as alkylating agent or blends of IPA and propylene, in any case remains exothermic in spite of the presence of IPA and in order to maintain the temperature within a preferred range and reduce the by-production of polyalkylated aromatic compounds, the catalyst can be arranged in the reactor in various layers inside a fixed bed reactor.

A quench is effected between one layer and another with inert solvents and part of the benzene and/or part of the alkylating agent, isopropyl alcohol or blends of isopropyl alcohol/propylene.

By thus operating, it is possible to obtain high benzene/alkylating agent ratios on the single layer, without increasing the same overall ratio, with an evident advantage with respect to the selectivity to cumene and consequently the separation operations downstream of the reaction section.

The temperature control can be effected not only by effecting a quench of the reagents and/or inert products, but also by inter-cooling between the layers.

The alkylation reaction can be conveniently carried out in two or more reactors in series, inter-cooled to control the temperature. The feeding of the isopropyl alcohol, optionally mixed with propylene, and/or benzene can be suitably divided between the various reactors and different layers of the reactor, i.e. the alkylating agent and the benzene are added in more than one step.

The objectives of the present invention also include a process for preparing phenol which comprises the following steps:
1) alkylation of benzene with isopropanol, or a blend of isopropanol and propylene, to give cumene and water, comprising effecting said alkylation reaction completely in gaseous phase and in the presence of a catalytic system containing a zeolite belonging to the MTW family;
2) oxidation of the cumene thus obtained to cumyl hydroperoxide;
3) treatment of the cumyl hydroperoxide with acids in order to obtain a mixture of phenol and acetone;
4) hydrogenation of the acetone to isopropanol which is recycled to step (1).

Step (1) is carried out in accordance with the above-mentioned aspects of the alkylation process of the present invention. In step (2) the cumene deriving from step (1) is oxidized with air to give cumyl hydroperoxide, which in turn is treated with an acid to give a mixture of phenol and acetone which is fractionated to separate the phenol from the acetone. In step (3), the acetone obtained in step (2) is partially or totally hydrogenated to isopropyl alcohol which is recycled to step (1).

According to a preferred aspect, at the end of the first step, after separating the desired product, cumene, by fractionation, which passes to the following oxidation step, the remaining fraction of polyisopropylbenzenes is used in a separate step for a transalkylation reaction with benzene to recover further cumene.

The transalkylation reaction can be carried out using any of the catalysts known to experts in the field for the transalkylation of polyisopropylbenzenes with benzene, in particular it can be effected in the presence of beta zeolite or a catalyst based on beta zeolite, in particular prepared according to what is described in EP 687500 and EP 847802. The temperature conditions for the transalkylation reaction can be selected from 100° C. to 350° C., the pressure is selected from 10 to 50 atm and the WHSV ranges from 0.1 hours$^{-1}$ to 200 hours$^{-1}$. These conditions are in accordance with what is described in EP 687500.

In step (2) therefore, the cumene deriving from step (1), and optionally from the transalkylation step, is oxidized to cumyl hydroperoxide. The cumyl hydroperoxide is then transformed to phenol and acetone. The oxidation to cumyl hydroperoxide and the subsequent transformation to phenol can be effected for example as described in U.S. Pat. No. 5,017,729. In the last step, part or all of the acetone obtained as by-product from step (2) is hydrogenated to isopropyl alcohol and is re-fed to the initial step.

The hydrogenation reaction of acetone to isopropanol is already known and is carried out using catalysts based on Nickel Raney, nickel-copper, copper-chromium, copper-zinc or based on metals of the platinum group for example platinum, palladium, ruthenium, rhodium.

A catalyst based on Nickel Raney or copper-chromium is preferably used.

The conditions under which the hydrogenation reaction of the acetone takes place are described, among others, in U.S. Pat. No. 5,015,786 or U.S. Pat. No. 5,017,729.

A remarkable aspect of the processes claimed herein and in particular of the alkylation step of benzene with isopropanol or blends of propylene and isopropanol, in gas phase and in the presence of a catalyst containing MTW zeolite, is the considerable flexibility of the re-use of the acetone, co-produced with phenol, from which isopropyl alcohol is obtained by reduction with hydrogen.

This flexibility is in fact made possible by the use, in our process, of the catalyst based on MTW zeolite which guarantees the absence of the reduction phenomena of the performances and rapid deactivation typical of solid acid catalysts due to the presence of water formed by the use of isopropyl alcohol as alkylating agent of benzene.

The following examples have the sole purpose of illustrating the invention claimed herein without limiting its objectives in any way.

EXAMPLE 1

An alkylation test of benzene is carried out with isopropyl alcohol, using the experimental device described below.

The experimental device consists of tanks for the benzene and isopropyl alcohol reagents, feeding pumps of the reagents to the reactor, preheating units of the reagents, steel reactor situated inside an electric heating oven, regulation loop of the temperature inside the reactor, regulation loop of the pressure inside the reactor, cooling agent of the reactor effluent and collection system of the liquid and gaseous products.

In particular, the reactor consists of a cylindrical steel tube with a mechanical sealing system and a diameter equal to about 2 cm.

Along the greater axis of the reactor there is a thermometric cavity having a diameter equal to 1 mm containing in its interior a thermocouple free to slide along the greater axis of the reactor.

A catalyst containing ZSM-12 zeolite prepared as described in Example 2 of U.S. 2003/0069459 is charged into the reactor.

A quantity of inert material is charged above and below the catalytic bed to complete the bed.

The benzene and isopropanol (IPA) reagents are fed to the reactor—preheated and premixed in an appropriate mixer—with up flow.

The reaction products are analyzed via gas chromatography. The reaction conditions under which the test is carried out are the following:
Reaction temperature: 190° C.
Reaction pressure: 8 bar
WHSV: 4 hours$^{-1}$
[Benzene]/[IPA] in the feeding: 3.25 moles/moles These conditions ensure that the reagents are in gaseous phase and the products partially in liquid phase.

The attribution of the physical state of the reagent mixture is effected by both comparison with the phase diagrams existing for the components and the mixtures in question, and also by calculation, adopting the RKS state equation (Soave. G. Chem. Eng. Sci 27, 1197, (1972)). The interaction parameters for this equation are obtained from the regression of the experimental data of literature relating to the liquid-vapour equilibria and the reciprocal solubilities of the hydrocarbon-water mixtures (C. C. Li, J. J. McKetta July Chem. Eng. Data 8 271-275 (1963) and C. Tsonopoulos, G. M. Wilson ALCHE Journel 29, 990-999, (1983)).

The reaction system to which the above equation is applied is assimilated, with respect to the compositions, to the system [benzene]/[propylene]=3.25 and
[benzene]/[water]=3.25

The concentration of total water present in the system with the complete conversion of the isopropyl alcohol reagent is equal to about 5%.

FIG. 1 indicates the trend of the molar selectivity [Ar]/[IPA] (Cumene+Diisopropylbenzenes+Triisopropylbenzenes with respect to the total of IPA converted) in relation to the productivity of the catalyst expressed in Kg cumene/Kg ZSM-12 zeolite and the trend of the molar selectivity [Cum]/[IPA] (Cumene with respect to the total of IPA converted) in relation to the productivity of the catalyst in Kg cumene/Kg ZSM-12 zeolite.

For the whole duration of the test (about 620 hours) no signs of deactivation of the catalyst were observed, such as, for example, a drop in the conversion of the alcohol (not shown in FIG. 1 but quantitative for the whole duration of the test) or an increase in the polyalkylated fraction.

The selectivities during the whole test, in fact, remained unaltered with values equal to about 82% for the selectivity [Cum]/[IPA] and about 98.8% for the selectivity [Ar]/[IPA].

EXAMPLE 2

Comparative

The results obtained in the previous example are compared with those obtained using a catalyst containing beta zeolite prepared as described in example 4 of EP 847802.

Both catalysts, of Example 1 and comparative Example 2 contain about 50% of active phase.

The same experimental equipment described in Example 1 is used, under the same operating conditions which ensure that the reagents are in gaseous phase and the products partially in liquid phase.

The attribution of the physical state of the reagent mixture is effected as previously described in Example 1.

FIG. 2 indicates the trend of the molar selectivity [Ar]/[IPA] and the molar selectivity [Cum]/[IPA] in relation to the productivity of the catalyst.

After about 160 hours of running, the conversion of the alcohol had already been reduced by 2.5%. This value clearly demonstrates, under the same operating conditions, the greater stability with time of the catalyst containing ZSM-12 in the alkylation of benzene with isopropanol in gas phase and therefore its higher productivity.

The catalyst containing ZSM-12, object of the invention, is more selective with respect to the total useful aromatic products (about 0.5% more) and a comparison with the trends indicated in FIGS. 1 and 2 also shows that the catalyst containing ZSM-12, object of the invention, is much more selective with respect to cumene (about 20% more).

The invention claimed is:

1. A process for the alkylation of benzene with isopropanol, or a blend of isopropanol and propylene, the process comprising effecting the alkylation reaction under temperature and pressure conditions corresponding to complete gas phase of the reagents and at least partial liquid phase of the reaction products, in the presence of a catalytic system comprising a zeolite belonging to the MTW family.

2. The process according to claim 1, wherein the MTW zeolite is a ZSM-12 zeolite.

3. The process according to claim 1, wherein the zeolite is in a form in which a cationic site present in the zeolite is at least 50% occupied by hydrogen ions.

4. The process according to claim 1, wherein the zeolite is in a form bound with a ligand.

5. The process according to claim 4, wherein the ligand is selected from the group consisting of alumina, silica, a silico-aluminate, titania, zirconia and clay.

6. The process according to claim 1, wherein the effecting is at a temperature of from 150 to 230° C. and at a pressure of from 1 to 20 bar.

7. The process according to claim 6, wherein the pressure is lower than 10 bar.

8. The process according to claim 1, wherein a molar ratio between benzene and isopropanol, or between benzene and a blend of isopropanol and propylene, is from 2 to 10.

9. The process according to claim 8, wherein the molar ratio is from 2 to 4.

10. The process according to claim 1, wherein, when the alkylating mixture comprises isopropanol and propylene, the reaction is carried out with a molar ratio between isopropanol and propylene of from 10 to 0.01.

11. The process according to claim 10, wherein the reaction is carried out with a molar ratio between isopropanol and propylene of from 5 to 0.1.

12. The process according to claim 1, wherein the catalytic system comprises phosphorous.

13. The process according to claim 12, wherein the catalytic system comprises phosphorous in a quantity lower than 3% by weight with respect to a total weight of the catalytic composition.

14. A process for preparing phenol, comprising:
alkylating benzene with isopropanol, and optionally propylene, to obtain cumene and water;
oxidizing the cumene thus obtained to cumyl hydroperoxide;
treating the cumyl hydroperoxide with acids in order to obtain a mixture of phenol and acetone;
hydrogenating the acetone to isopropanol,
wherein the alkylating is carried out by the process according to claim 1.

15. The process according to claim 1, further comprising:
cooling;
demixing of an organic phase from an aqueous phase;
removing of the aqueous phase; and
subsequently re-feeding the organic phase of the reaction effluent to the same reaction.

16. The process according to claim 1, further comprising:
separating polyalkylated products present in the reaction effluent deriving from the alkylation reaction in a specific fractionation section; and
sending the separated polyalkylated products to a transalkylation section with benzene.

17. A process for the alkylation of benzene with isopropanol, or a blend of isopropanol and propylene, the process comprising effecting the alkylation reaction under temperature and pressure conditions corresponding to complete gas phase of the reagents in the presence of a catalytic system comprising a zeolite belonging to the MTW family,
wherein
the zeolite is in a form bound with a ligand, and
the ligand is selected from the group consisting of alumina, silica, a silico-aluminate, titania, zirconia, and clay.

18. The process according to claim 17, wherein the MTW zeolite is a ZSM-12 zeolite.

* * * * *